United States Patent
Schwab et al.

(10) Patent No.: US 9,801,747 B2
(45) Date of Patent: Oct. 31, 2017

(54) NON-INFLATABLE GASTRIC IMPLANTS AND SYSTEMS

(71) Applicant: Apollo Endosurgery, Inc., Austin, TX (US)

(72) Inventors: Justin J. Schwab, Santa Barbara, CA (US); Mitchell H. Babkes, Santa Clarita, CA (US); Jason Metzner, Covington, WA (US); Zachary P. Dominguez, Santa Barbara, CA (US)

(73) Assignee: APOLLO ENDOSURGERY US, INC., Austin, TX (US)

( * ) Notice: Subject to any disclaimer, the term of this patent is extended or adjusted under 35 U.S.C. 154(b) by 52 days.

(21) Appl. No.: 14/608,538

(22) Filed: Jan. 29, 2015

(65) Prior Publication Data
US 2015/0142044 A1    May 21, 2015

Related U.S. Application Data

(62) Division of application No. 13/276,904, filed on Oct. 19, 2011, now abandoned.
(Continued)

(51) Int. Cl.
*A61M 29/00* (2006.01)
*A61F 5/00* (2006.01)

(52) U.S. Cl.
CPC .......... *A61F 5/0036* (2013.01); *A61F 5/0003* (2013.01); *A61F 5/003* (2013.01);
(Continued)

(58) Field of Classification Search
CPC .... A61F 5/0033; A61F 5/0036; A61F 5/0003; A61F 5/0013; A61F 5/0076;
(Continued)

(56) References Cited

U.S. PATENT DOCUMENTS

| 1,702,974 A | 2/1929 | MacDonald |
| 2,087,604 A | 7/1937 | Mosher |

(Continued)

FOREIGN PATENT DOCUMENTS

| CN | 1250382 A | 4/2000 |
| CN | 1367670 A | 9/2002 |

(Continued)

OTHER PUBLICATIONS

'Living With the Bib/BioEnterics Intragastric Balloon Program,' Inamed Health; 1-10 Patient Information Brochure; pp.; May 1, 2005.

(Continued)

*Primary Examiner* — Richard Louis
(74) *Attorney, Agent, or Firm* — Gordon & Jacoboson, P.C.

(57) ABSTRACT

A variety of passive intragastric implant devices for obesity treatment are disclosed. Such passive devices do not autonomously change shape, but instead react within the stomach to induce satiety. The devices may take up volume within the stomach, thus reducing the intake capacity. Additionally, the devices may contact areas within the stomach, such as the cardia surrounding the esophageal sphincter, or the greater and lesser curvatures in the middle of the stomach, to stimulate satiety-inducing nerves. Some devices may combine two or more of these satiety-inducing features. Methods of implant are disclosed including compressing the devices within a delivery tube and transorally advancing the devices through the esophagus to be deployed within the stomach. Removal of the devices occurs in the reverse.

18 Claims, 10 Drawing Sheets

Related U.S. Application Data

(60) Provisional application No. 61/485,009, filed on May 11, 2011, provisional application No. 61/394,592, filed on Oct. 19, 2010.

(52) U.S. Cl.
CPC .......... *A61F 5/0013* (2013.01); *A61F 5/0033* (2013.01); *A61F 5/0076* (2013.01); *A61F 5/0086* (2013.01); *A61F 5/0079* (2013.01); *A61F 5/0089* (2013.01); *Y10T 24/4453* (2015.01); *Y10T 24/44342* (2015.01); *Y10T 24/44564* (2015.01)

(58) Field of Classification Search
CPC .... A61F 5/0086; A61F 5/0079; A61F 5/0089; Y10T 24/44564; Y10T 24/4453; Y10T 24/44342
See application file for complete search history.

(56) References Cited

U.S. PATENT DOCUMENTS

| | | |
|---|---|---|
| 2,163,048 A | 6/1939 | McKee |
| 2,619,138 A | 11/1952 | Marler |
| 3,667,081 A | 6/1972 | Burger |
| 3,719,973 A | 3/1973 | Bell |
| 3,840,018 A | 10/1974 | Heifetz |
| 3,919,724 A | 11/1975 | Sanders |
| 4,118,805 A | 10/1978 | Reimels |
| 4,364,379 A | 12/1982 | Finney |
| 4,416,267 A | 11/1983 | Garren |
| 4,430,392 A | 2/1984 | Kelley |
| 4,485,805 A | 12/1984 | Foster |
| 4,545,367 A | 10/1985 | Tucci |
| 4,586,501 A | 5/1986 | Claracq |
| 4,592,355 A | 6/1986 | Antebi |
| 4,598,699 A | 7/1986 | Garren |
| 4,607,618 A | 8/1986 | Angelchik |
| 4,636,213 A | 1/1987 | Pakiam |
| 4,648,383 A | 3/1987 | Angelchik |
| 4,694,827 A | 9/1987 | Weiner |
| 4,723,547 A | 2/1988 | Kullas |
| 4,739,758 A | 4/1988 | Lai |
| 4,773,432 A | 9/1988 | Rydell |
| 4,774,956 A | 10/1988 | Kruse |
| 4,844,068 A | 7/1989 | Arata |
| 4,881,939 A | 11/1989 | Newman |
| 4,899,747 A | 2/1990 | Garren |
| 4,925,446 A | 5/1990 | Garay |
| 4,930,535 A | 6/1990 | Rinehold |
| 4,950,258 A | 8/1990 | Kawai |
| 4,969,899 A | 11/1990 | Cox |
| 5,074,868 A | 12/1991 | Kuzmak |
| 5,084,061 A | 1/1992 | Gau |
| 5,104,404 A | 4/1992 | Wolff |
| 5,211,371 A | 5/1993 | Coffee |
| 5,226,429 A | 7/1993 | Kuzmak |
| 5,255,690 A | 10/1993 | Keith |
| 5,259,399 A | 11/1993 | Brown |
| 5,289,817 A | 3/1994 | Williams |
| 5,308,324 A | 5/1994 | Hammerslag |
| 5,312,343 A | 5/1994 | Krog |
| 5,449,368 A | 9/1995 | Kuzmak |
| 5,514,176 A | 5/1996 | Bosley |
| 5,527,340 A | 6/1996 | Vogel |
| 5,540,701 A | 7/1996 | Sharkey |
| 5,547,458 A | 8/1996 | Ortiz |
| 5,601,604 A | 2/1997 | Vincent |
| 5,658,298 A | 8/1997 | Vincent |
| 5,693,014 A | 12/1997 | Abele |
| 5,725,507 A | 3/1998 | Petrick |
| 5,748,200 A | 5/1998 | Funahashi |
| 5,776,160 A | 7/1998 | Pasricha |
| 5,819,749 A | 10/1998 | Lee |
| 5,820,584 A | 10/1998 | Crabb |
| RE36,176 E | 3/1999 | Kuzmak |
| 5,938,669 A | 8/1999 | Klaiber |
| 6,074,341 A | 6/2000 | Anderson |
| 6,102,678 A | 8/2000 | Peclat |
| 6,102,897 A | 8/2000 | Lang |
| 6,102,922 A | 8/2000 | Jakobsson |
| 6,152,922 A | 11/2000 | Ouchi |
| 6,183,492 B1 | 2/2001 | Hart |
| 6,264,700 B1 | 7/2001 | Kilcoyne |
| 6,290,575 B1 | 9/2001 | Shipp |
| 6,322,538 B1 | 11/2001 | Elbert |
| 6,450,946 B1 | 9/2002 | Forsell |
| 6,454,699 B1 | 9/2002 | Forsell |
| 6,454,785 B2 | 9/2002 | DeHoyosGarza |
| 6,464,628 B1 | 10/2002 | Forsell |
| 6,470,892 B1 | 10/2002 | Forsell |
| 6,503,264 B1 | 1/2003 | Birk |
| 6,511,490 B2 | 1/2003 | Robert |
| 6,540,789 B1 | 4/2003 | Silverman |
| 6,547,801 B1 | 4/2003 | Dargent |
| 6,579,301 B1 | 6/2003 | Bales |
| 6,629,776 B2 | 10/2003 | Bell |
| 6,675,809 B2 | 1/2004 | Stack |
| 6,682,473 B1 | 1/2004 | Matsuura |
| 6,733,512 B2 | 5/2004 | McGhan |
| 6,733,513 B2 | 5/2004 | Boyle |
| 6,746,460 B2 | 6/2004 | Gannoe |
| 6,776,783 B1 | 8/2004 | Frantzen |
| 6,840,257 B2 | 1/2005 | Dario |
| 6,845,776 B2 | 1/2005 | Stack |
| 6,905,471 B2 | 6/2005 | Leivseth |
| 6,960,233 B1 | 11/2005 | Berg |
| 6,981,978 B2 | 1/2006 | Gannoe |
| 6,981,980 B2 | 1/2006 | Sampson |
| 6,994,095 B2 | 2/2006 | Burnett |
| 7,008,419 B2 | 3/2006 | Shadduck |
| 7,020,531 B1 | 3/2006 | Colliou |
| 7,033,384 B2 | 4/2006 | Gannoe |
| 7,037,344 B2 | 5/2006 | Kagan |
| 7,056,305 B2 | 6/2006 | GarzaAlvarez |
| 7,090,699 B2 | 8/2006 | Geitz |
| 7,214,233 B2 | 5/2007 | Gannoe |
| 7,220,237 B2 | 5/2007 | Gannoe |
| 7,220,284 B2 | 5/2007 | Kagan |
| 7,223,277 B2 | 5/2007 | DeLegge |
| 7,320,696 B2 | 1/2008 | Gazi |
| 7,347,875 B2 | 3/2008 | Levine |
| 7,354,454 B2 | 4/2008 | Stack |
| 7,476,256 B2 | 1/2009 | Meade |
| 7,510,559 B2 | 3/2009 | Deem |
| 7,608,114 B2 | 10/2009 | Levine |
| 7,628,442 B1 | 12/2009 | Spencer |
| 7,682,330 B2 | 3/2010 | Meade |
| 7,695,446 B2 | 4/2010 | Levine |
| 7,699,863 B2 | 4/2010 | Marco |
| 7,753,870 B2 | 7/2010 | Demarais |
| 7,771,382 B2 | 8/2010 | Levine |
| 7,794,447 B2 | 9/2010 | Dann |
| 7,815,589 B2 | 10/2010 | Meade |
| 7,837,643 B2 | 11/2010 | Levine |
| 7,841,503 B2 | 11/2010 | Sonnenschein |
| 7,883,525 B2 | 2/2011 | DeLegge |
| 7,931,693 B2 | 4/2011 | Binmoeller |
| 7,981,162 B2 | 7/2011 | Stack |
| 8,029,455 B2 | 10/2011 | Stack |
| 8,032,223 B2 | 10/2011 | Imran |
| 8,075,582 B2 | 12/2011 | Lointier |
| 8,162,969 B2 | 4/2012 | Brister |
| 8,187,297 B2 | 5/2012 | Makower |
| 8,216,266 B2 | 7/2012 | Hively |
| 2002/0019577 A1 | 2/2002 | Arabia |
| 2002/0055757 A1 | 5/2002 | Torre |
| 2002/0095181 A1 | 7/2002 | Beyar |
| 2002/0139208 A1 | 10/2002 | Yatskov |
| 2002/0183782 A1 | 12/2002 | Tsugita |
| 2003/0014127 A1 | 1/2003 | Talja |
| 2003/0040804 A1 | 2/2003 | Stack |
| 2003/0045896 A1 | 3/2003 | Murphy |

(56) References Cited

U.S. PATENT DOCUMENTS

| | | |
|---|---|---|
| 2003/0073880 A1 | 4/2003 | Polsky |
| 2003/0074054 A1 | 4/2003 | Duerig |
| 2003/0100822 A1 | 5/2003 | Lew |
| 2003/0106761 A1 | 6/2003 | Taylor |
| 2003/0109935 A1* | 6/2003 | Geitz ............. A61F 5/0036 623/23.65 |
| 2003/0144575 A1 | 7/2003 | Forsell |
| 2003/0153905 A1 | 8/2003 | Edwards |
| 2003/0158570 A1 | 8/2003 | Ferrazzi |
| 2004/0044357 A1 | 3/2004 | Gannoe |
| 2004/0092892 A1 | 5/2004 | Kagan |
| 2004/0117031 A1 | 6/2004 | Stack |
| 2004/0122452 A1 | 6/2004 | Deem |
| 2004/0122453 A1 | 6/2004 | Deem |
| 2004/0143342 A1 | 7/2004 | Stack |
| 2004/0148034 A1 | 7/2004 | Kagan |
| 2004/0172142 A1 | 9/2004 | Stack |
| 2004/0186503 A1 | 9/2004 | DeLegge |
| 2005/0033332 A1 | 2/2005 | Burnett |
| 2005/0049718 A1 | 3/2005 | Dann |
| 2005/0055039 A1 | 3/2005 | Burnett |
| 2005/0085923 A1 | 4/2005 | Levine |
| 2005/0096692 A1 | 5/2005 | Linder |
| 2005/0110280 A1 | 5/2005 | Guy |
| 2005/0131485 A1 | 6/2005 | Knudson |
| 2005/0190070 A1 | 9/2005 | Rudduck |
| 2005/0192614 A1 | 9/2005 | Binmoeller |
| 2005/0192615 A1 | 9/2005 | Torre |
| 2005/0197714 A1 | 9/2005 | Sayet |
| 2005/0226682 A1* | 10/2005 | Chersky ............. F16M 11/14 403/56 |
| 2005/0228504 A1 | 10/2005 | Demarais |
| 2005/0240279 A1 | 10/2005 | Kagan |
| 2005/0250979 A1 | 11/2005 | Coe |
| 2005/0256533 A1 | 11/2005 | Roth |
| 2005/0261711 A1 | 11/2005 | Okada |
| 2005/0267595 A1* | 12/2005 | Chen ............. A61F 5/003 623/23.65 |
| 2005/0267596 A1 | 12/2005 | Chen |
| 2005/0273060 A1 | 12/2005 | Levy |
| 2005/0277975 A1 | 12/2005 | Saadat |
| 2006/0020278 A1 | 1/2006 | Burnett |
| 2006/0025799 A1 | 2/2006 | Basu |
| 2006/0069403 A1 | 3/2006 | Shalon |
| 2006/0106288 A1 | 5/2006 | Roth |
| 2006/0142700 A1 | 6/2006 | Sobelman |
| 2006/0178691 A1 | 8/2006 | Binmoeller |
| 2006/0190019 A1 | 8/2006 | Gannoe |
| 2006/0217762 A1 | 9/2006 | Maahs |
| 2006/0229702 A1 | 10/2006 | Agnew |
| 2006/0252983 A1 | 11/2006 | Lembo |
| 2007/0010864 A1 | 1/2007 | Dann |
| 2007/0016262 A1 | 1/2007 | Gross |
| 2007/0021761 A1 | 1/2007 | Phillips |
| 2007/0078476 A1 | 4/2007 | Hull |
| 2007/0083224 A1 | 4/2007 | Hively |
| 2007/0100368 A1 | 5/2007 | Quijano |
| 2007/0118168 A1 | 5/2007 | Lointier |
| 2007/0135803 A1 | 6/2007 | Belson |
| 2007/0135829 A1 | 6/2007 | Paganon |
| 2007/0147170 A1 | 6/2007 | Hood |
| 2007/0149994 A1 | 6/2007 | Sosnowski |
| 2007/0156013 A1 | 7/2007 | Birk |
| 2007/0156248 A1 | 7/2007 | Marco |
| 2007/0173881 A1 | 7/2007 | Birk |
| 2007/0185374 A1 | 8/2007 | Kick |
| 2007/0239284 A1 | 10/2007 | Skerven |
| 2007/0250020 A1 | 10/2007 | Kim |
| 2007/0265598 A1 | 11/2007 | Karasik |
| 2007/0276428 A1* | 11/2007 | Haller et al. ............. 606/192 |
| 2007/0288033 A1 | 12/2007 | Murature |
| 2007/0293716 A1 | 12/2007 | Baker |
| 2008/0015618 A1 | 1/2008 | Sonnenschein |
| 2008/0058840 A1 | 3/2008 | Albrecht |
| 2008/0058887 A1 | 3/2008 | Griffin |
| 2008/0065122 A1 | 3/2008 | Stack |
| 2008/0071305 A1 | 3/2008 | DeLegge |
| 2008/0097513 A1 | 4/2008 | Kaji |
| 2008/0109027 A1* | 5/2008 | Chen ............. A61F 5/003 606/191 |
| 2008/0121765 A1* | 5/2008 | Fetzer ............. A61B 90/50 248/122.1 |
| 2008/0167606 A1 | 7/2008 | Dann |
| 2008/0172079 A1 | 7/2008 | Birk |
| 2008/0208240 A1 | 8/2008 | Paz |
| 2008/0208241 A1 | 8/2008 | Weiner |
| 2008/0221595 A1 | 9/2008 | Surti |
| 2008/0228205 A1 | 9/2008 | Sharkey |
| 2008/0234718 A1 | 9/2008 | Paganon |
| 2008/0234834 A1 | 9/2008 | Meade |
| 2008/0243071 A1 | 10/2008 | Quijano |
| 2008/0243166 A1 | 10/2008 | Paganon |
| 2008/0249635 A1 | 10/2008 | Weitzner |
| 2008/0255601 A1 | 10/2008 | Birk |
| 2008/0255678 A1 | 10/2008 | Cully |
| 2008/0262529 A1 | 10/2008 | Jacques |
| 2008/0306506 A1 | 12/2008 | Leatherman |
| 2009/0012553 A1 | 1/2009 | Swain |
| 2009/0082644 A1 | 3/2009 | Li |
| 2009/0093767 A1 | 4/2009 | Kelleher |
| 2009/0093837 A1 | 4/2009 | Dillon |
| 2009/0131968 A1 | 5/2009 | Birk |
| 2009/0132031 A1 | 5/2009 | Cook |
| 2009/0149879 A1 | 6/2009 | Dillon |
| 2009/0177215 A1 | 7/2009 | Stack |
| 2009/0198210 A1 | 8/2009 | Burnett |
| 2009/0216337 A1 | 8/2009 | Egan |
| 2009/0259246 A1 | 10/2009 | Eskaros |
| 2009/0275973 A1 | 11/2009 | Chen |
| 2009/0287231 A1 | 11/2009 | Brooks |
| 2009/0299327 A1 | 12/2009 | Tilson |
| 2009/0299486 A1 | 12/2009 | Shohat |
| 2009/0312597 A1 | 12/2009 | Bar |
| 2009/0326433 A1* | 12/2009 | Albrecht et al. ............. 604/19 |
| 2010/0030017 A1 | 2/2010 | Baker |
| 2010/0049224 A1* | 2/2010 | Vargas ............. A61F 5/0036 606/153 |
| 2010/0081991 A1 | 4/2010 | Swisher |
| 2010/0082047 A1 | 4/2010 | Cosgrove |
| 2010/0087843 A1 | 4/2010 | Bertolote |
| 2010/0100079 A1 | 4/2010 | Berkcan |
| 2010/0100115 A1 | 4/2010 | Soetermans |
| 2010/0121371 A1 | 5/2010 | Brooks |
| 2010/0168782 A1 | 7/2010 | Hancock |
| 2010/0168783 A1 | 7/2010 | Murature |
| 2010/0174307 A1 | 7/2010 | Birk |
| 2010/0198249 A1 | 8/2010 | Sabliere |
| 2010/0234937 A1 | 9/2010 | Wang |
| 2010/0249822 A1 | 9/2010 | Nihalani |
| 2010/0249825 A1 | 9/2010 | Nihalani |
| 2010/0256775 A1 | 10/2010 | Belhe |
| 2010/0256776 A1 | 10/2010 | Levine |
| 2010/0261390 A1 | 10/2010 | Gardner |
| 2010/0274194 A1 | 10/2010 | Sobelman |
| 2010/0286628 A1 | 11/2010 | Gross |
| 2010/0305590 A1 | 12/2010 | Holmes |
| 2010/0331756 A1 | 12/2010 | Meade |
| 2010/0332000 A1 | 12/2010 | Forsell |
| 2011/0009897 A1 | 1/2011 | Forsell |
| 2011/0106113 A1 | 5/2011 | Tavakkolizadeh |
| 2011/0307075 A1 | 12/2011 | Sharma |
| 2012/0022561 A1 | 1/2012 | Forsell |
| 2012/0095483 A1 | 4/2012 | Babkes |
| 2012/0221037 A1 | 8/2012 | Birk |
| 2012/0289992 A1* | 11/2012 | Quijano ............. A61F 5/0003 606/192 |

FOREIGN PATENT DOCUMENTS

| | | |
|---|---|---|
| DE | 8804765 U1 | 5/1989 |
| DE | 102007025312 A1 | 11/2008 |
| EP | 1396242 | 3/2004 |
| EP | 1396243 | 3/2004 |

(56) References Cited

FOREIGN PATENT DOCUMENTS

| | | |
|---|---|---|
| EP | 1397998 A1 | 3/2004 |
| EP | 1774929 A2 | 4/2007 |
| EP | 2095798 | 9/2009 |
| FR | 2797181 | 2/2001 |
| FR | 2823663 | 10/2002 |
| FR | 2852821 A1 | 10/2004 |
| FR | 2855744 | 12/2004 |
| FR | 2892297 A1 | 4/2007 |
| FR | 2941617 A1 | 8/2010 |
| GB | 2086792 A | 5/1982 |
| JP | 63264078 | 10/1988 |
| JP | S63279854 A | 11/1988 |
| JP | 1049572 A | 2/1989 |
| WO | 0015158 | 3/2000 |
| WO | 0032092 | 6/2000 |
| WO | 0110359 | 2/2001 |
| WO | 0149245 | 7/2001 |
| WO | 0166166 A2 | 9/2001 |
| WO | 0235980 A2 | 5/2002 |
| WO | 03055419 A1 | 7/2003 |
| WO | 03105732 | 12/2003 |
| WO | 2004019671 A2 | 3/2004 |
| WO | 2005007231 A1 | 1/2005 |
| WO | 2005094257 A2 | 10/2005 |
| WO | 2005097012 A2 | 10/2005 |
| WO | 2005110280 A2 | 11/2005 |
| WO | 2006020370 | 2/2006 |
| WO | 2006044640 A1 | 4/2006 |
| WO | 2006063593 A2 | 6/2006 |
| WO | 2006090018 A1 | 8/2006 |
| WO | 2006111961 A2 | 10/2006 |
| WO | 2006118744 A1 | 11/2006 |
| WO | 2007027812 A2 | 3/2007 |
| WO | 2007053556 A1 | 5/2007 |
| WO | 2007076021 A2 | 7/2007 |
| WO | 2007092390 A2 | 8/2007 |
| WO | 2007110866 A2 | 10/2007 |
| WO | 2008101048 A2 | 8/2008 |
| WO | 2008112894 A1 | 9/2008 |
| WO | 2008132745 A2 | 11/2008 |
| WO | 2010042062 A1 | 4/2010 |
| WO | 2010074712 A2 | 7/2010 |
| WO | 2010087757 A1 | 8/2010 |
| WO | 2010117641 A2 | 10/2010 |

OTHER PUBLICATIONS

Baggio et al. 'Biology of Integrins: GLP-1 and GIP'; Gastroenterology; V. 132; pp. 2131-2157; 2007.

Berne et al; 'Physiology'; V. 5; pp. 55-57, 210, 428, 540, 554, 579, 584, 591; 2004.

BIB Bioenterics Intragastric Balloon Program, 'Take Control of Your Weight and Your Life/The Solution for You,' Inamed Health, pp. 1-2; Jan. 19, 2004.

BIB Bioenterics Intragastric Balloon Program, 'Taking the Next Step/Take Control of Your Weight and Your Life,' Inamed Health, pp. 1-9; Apr. 29, 2004.

BIB Data Sheet Directions for Use, 'BioEnterics Intragastric Balloon System,' Inamed Health, 1-12 pp.; Rev 03, Feb. 2005.

Boulant et al.; 'Cholecystokinin in Transient Lower Oesophageal Sphincter Relation Due to Gastric Distension in Humans'; Gut; V. 40; pp. 575-581; 1997.

Bradjewin et al; 'Dose Ranging Study of the Effects of Cholecystokinin in Healthy Volunteers'; J. Psychiatr. Neurosci.; V. 16 (2); pp. 91-95; 1991.

Chaudhri; 'Can Gut Hormones Control Appetite and Prevent Obesity?' Diabetes Care; V. 31; Supp 2; pp. S284-S289; Feb. 2008.

Cohen et al.; 'Oxyntomodulin Suppresses Appetite and Reduces Food Intake in Humans'; J. Clin. Endocrinol. Metab.; V. 88; No. 10; pp. 4696-4701; 2003.

Dakin et al.; 'Oxyntomodulin Inhibits Food Intake in the Rat'; Endocrinology; V. 142; No. 10; pp. 4244-4250; 2001.

Dakin et al.; 'Peripheral Oxyntomodulin Reduces Food Intake and Body Weight gain in Rats'; Endocrinology; V. 145; No. 6; pp. 2687-2695; Jun. 2004.

Davison; 'Activation of Vagal-Gastric Mechanoreceptors by Cholecystokinin'; Proc. West. Pharmocol. Soc; V. 29; pp. 363-366; 1986.

Ekblad et al.; 'Distribution of Pancreatic Peptide and Peptide-YY'; Peptides; V. 23; pp. 251-261;2002.

Greenough et al.; 'Untangling the Effects of Hunger, Anxiety, and Nausea on Energy Intake During Intravenous Cholecystokinin Octapeptide (CCK-8) Infusion'; Physiology & Behavior; V. 65, No. 2; pp. 303-310; 1998.

Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.

Houpt; 'Gastrointestinal Factors in Hunger and Satiety'; Neurosci. and Behav. Rev.; V. 6; pp. 145-164; 1982.

Kissileff et al.; 'Peptides that Regulate Food Intake: Cholecystokinin and Stomach Distension Combine to Reduce Food Intake in Humans'; Am. J. Physiol. Regul. Integr. Comp. Physiol.; V. 285; pp. 992-998; 2003.

Naslund et al. 'Pranidal subcutaneous injections of glucagon-like peptide-1 cause weight loss in obese human subjects'; British Journal of Nutrition; V. 91; pp. 439-446; 2004.

Renshaw et al. 'Peptide YY: A Potential Therapy for Obesity'; Current Drug Targets; V. 6; pp. 171-179; 2005.

Verdich et al. 'A Meta-Analysis of the Effect of Glucagon-Like-Peptide-1 (7-36) Amide on ad Libitum Energy Intake in Humans'; J. Clin. Endocrinal. Metab. V. 86; pp. 4382-4389; Sep. 2001.

Wynne et al.; 'Subcutaneous Oxyntomodulin Reduces Body Weight in Overweight and Obese Subiects: A Double-Blind Randomized, Controlled Trial': Diabetes; V. 54; pp. 2390-2395; 2005.

Xanthakos et al.; 'Bariatric Surgery for Extreme Adolescent Obesity: Indications, Outcomes, and Physiologic Effects on the Gut-Brain Axis'; Pathophysiology; V. 15; pp. 135-146; 2008.

* cited by examiner

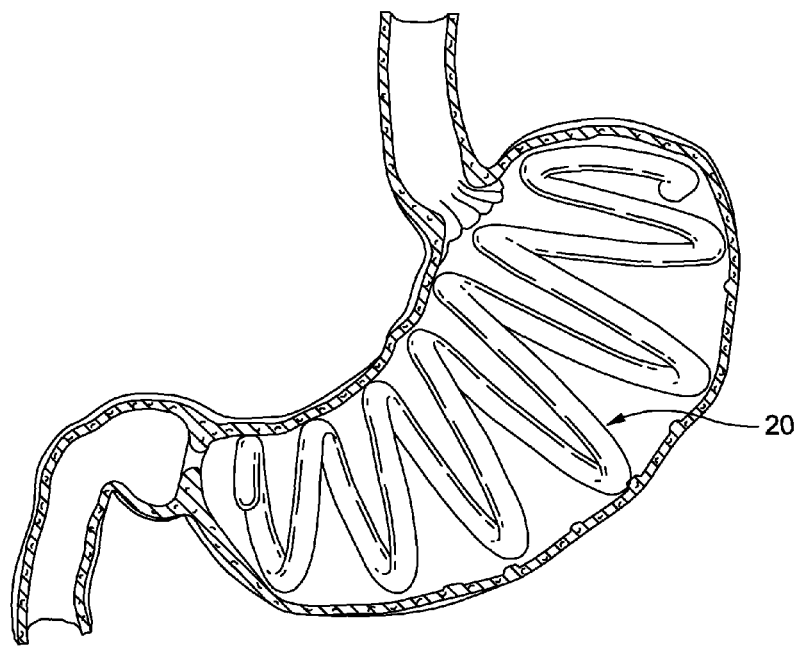
FIG. 1
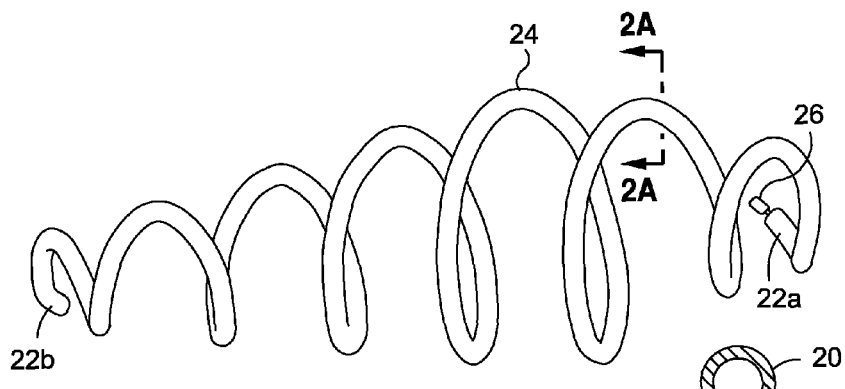
FIG. 2
FIG. 2A
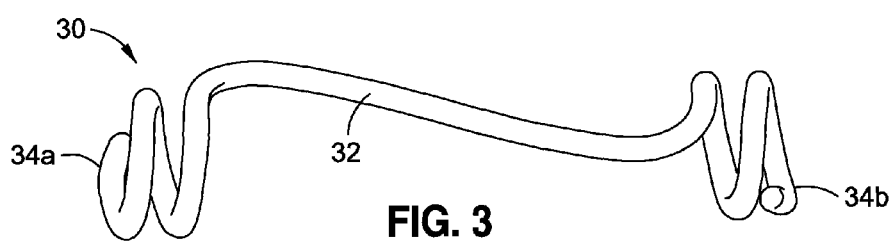
FIG. 3

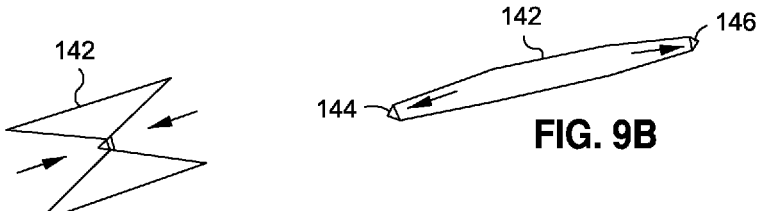
FIG. 9A
FIG. 9B
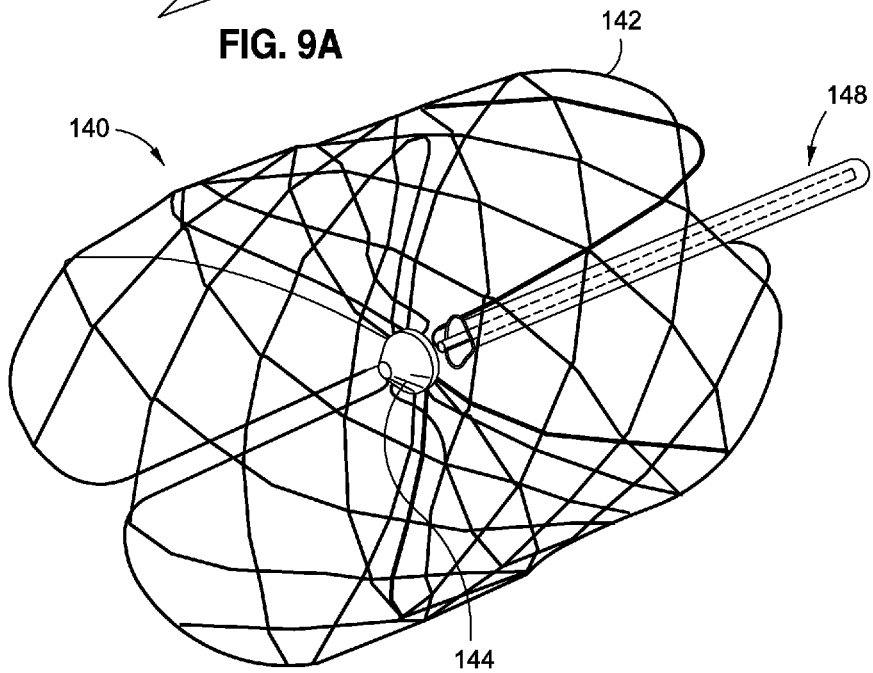
FIG. 8
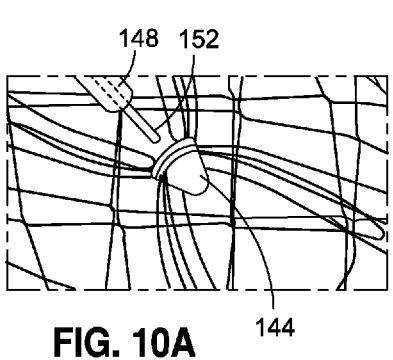
FIG. 10A
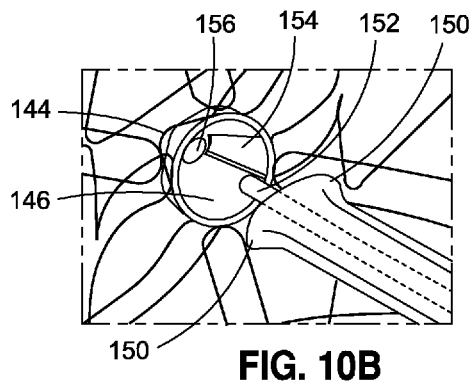
FIG. 10B

NON-INFLATABLE GASTRIC IMPLANTS AND SYSTEMS

RELATED APPLICATIONS

The present application is a divisional of U.S. Ser. No. 13/276,904, filed Oct. 19, 2011, which claims priority under 35 U.S.C. §119 to U.S. Provisional Application No. 61/485,009, filed May 11, 2011, and to 61/394,592, filed Oct. 19, 2010, the disclosures of all of which are incorporated by reference herein in their entireties.

FIELD OF THE INVENTION

The present invention is directed to intragastric devices used for the treatment of obesity, and in particular to devices and systems for placement in and adjacent to the stomach cavity.

BACKGROUND OF THE INVENTION

Over the last 50 years, obesity has been increasing at an alarming rate and is now recognized by leading government health authorities, such as the Centers for Disease Control (CDC) and National Institutes of Health (NIH), as a disease. In the United States alone, obesity affects more than 60 million individuals and is considered the second leading cause of preventable death. Worldwide, approximately 1.6 billion adults are overweight, and it is estimated that obesity affects at least 400 million adults.

Obesity is caused by a wide range of factors including genetics, metabolic disorders, physical and psychological issues, lifestyle, and poor nutrition. Millions of obese and overweight individuals first turn to diet, fitness and medication to lose weight; however, these efforts alone are often not enough to keep weight at a level that is optimal for good health. Surgery is another increasingly viable alternative for those with a Body Mass Index (BMI) of greater than 40. In fact, the number of bariatric surgeries in the United States was estimated to be about 400,000 in 2010.

Examples of surgical methods and devices used to treat obesity include the LAP-BAND® (Allergan Medical of Irvine, Calif.) gastric band and the LAP-BAND AP® (Allergan). However, surgery might not be an option for every obese individual; for certain patients, non-surgical therapies or minimal-surgery options are more effective or appropriate.

Intragastric balloons are also well known in the art as a means for treating obesity. One such inflatable intragastric balloon is described in U.S. Pat. No. 5,084,061 and is commercially available as the Orbera® System from Allergan Medical of Irvine, Calif. These devices are designed to provide therapy for moderately obese individuals who need to shed pounds in preparation for surgery, or as part of a dietary or behavioral modification program.

The Orbera® System, for example, consists of a silicone elastomer intragastric balloon that is inserted into the stomach in an empty or deflated state and thereafter filled (fully or partially) with a suitable fluid. The balloon occupies space in the stomach, thereby leaving less room for food and creating a feeling of satiety for the patient. Placement of the intragastric balloon is non-surgical, trans-oral, usually requiring no more than 20-30 minutes. The procedure is performed gastroscopically in an outpatient setting, typically using local anesthesia and sedation. Intragastric balloons typically are implanted for a finite period of time, up to six months. Removing the balloon requires deflation by puncturing with a gastroscopic instrument, and either aspirating the contents of the balloon and removing it, or allowing the fluid to pass into the patient's stomach. Clinical results with these devices show that for many obese patients, the intragastric balloons significantly help to control appetite and accomplish weight loss.

Some attempted solutions for weight loss by placing devices in the stomach result in unintended consequences. For instance, some devices tend to cause food and liquid to back up in the stomach, leading to symptoms of gastroesophageal reflux disease (GERD), a condition in which the stomach contents (food or liquid) leak backwards from the stomach into the esophagus. Also, the stomach acclimates to some gastric implant devices, leading to an expansion of stomach volume and consequent reduction in the efficacy of the device.

Therefore, despite many advances in the design of intragastric obesity treatment devices, there remains a need for improved devices that can be implanted for longer periods than before or otherwise address certain drawbacks of intragastric balloons and other such implants.

SUMMARY OF THE INVENTION

The present invention addresses the above-described problems by providing passive intragastric apparatuses and methods for inducing satiety and therefore treating obesity. Such passive devices do not autonomously change shape, but instead react within the stomach to induce satiety. The devices may take up volume within the stomach, thus reducing the intake capacity. Additionally, the devices may contact areas within the stomach, such as the cardia surrounding the esophageal sphincter, to stimulate satiety-inducing nerves. Also, a number of devices slow gastric emptying by blocking or otherwise impeding flow through the pyloric sphincter. Other devices delay digestion by providing a duodenal sleeve. A number of devices combine two or more of these satiety-inducing features. Methods of implant are disclosed including compressing the devices within a delivery tube and transorally advancing the devices through the esophagus to be deployed within the stomach. Removal of the devices occurs in the reverse.

In each of the following specific embodiments, the implants are formed of a material which permits it to be stretched into a substantially linear delivery configuration and that will resist degradation over a period of at least six months within the stomach.

In one aspect of the application, a passive intragastric obesity treatment implant comprises an elongated member having a relaxed configuration that forms a non-uniform diameter helix, with a middle coil of maximum diameter and end coils that are smaller than the middle coil. The relaxed configuration of the elongated member has a length and maximum diameter that generally fits within the stomach of an adult patient so as to span between the antrum and cardia walls and apply pressure to surrounding walls upon contraction thereof. The non-uniform diameter helix in a relaxed state preferably has a superior end adapted to be implanted at the cardia region and an inferior end adapted be implanted at the antrum region, and the middle coil of maximum diameter is offset so as to be closer to the superior end.

A further passive intragastric obesity treatment implant comprises an elongated member having a relaxed configuration that forms a non-uniform diameter helix with end coils and a middle region that is substantially without coils. The relaxed configuration has a length that generally fits within the stomach of an adult patient so as to span between the antrum and cardia walls and apply pressure surrounding walls upon contraction thereof. The non-uniform diameter helix in a relaxed state has a superior end adapted be implanted at the cardia region and an inferior end adapted to be implanted at the antrum region, and the coil diameter of the superior end is larger than the coil diameter of the inferior end.

In each of the two preceding implants, the elongated member may comprise a hollow plastic tube forming the non-uniform diameter helix, or may be a thin metal wire core covered with a soft outer layer. In one embodiment, opposite ends of the elongated member are slightly bent back inward toward an axis of the helix to avoid irritating pressure to stomach walls. The implant may further include a tab melt-molded into one end of the elongated member to serve as a grasping point for device removal.

Another aspect of the application is passive intragastric obesity treatment implant having a series of non-inflatable members each having a through bore. The members each having a male and a female mating connector which permits each member to connect with another member, each of the members being sized such that it can be easily implanted and removed through the esophagus, and the members together take up volume within the stomach of at least 400 ml. A tether is sized to pass through the through bores of the non-inflatable members, a distal end of the tether attaching to a distal one of the non-inflatable members such that the members can be pulled together by pulling the tether taut to cause the male and female mating connectors to couple, thus forming a relatively solid structure. Preferably, the male and female mating connectors of the members are configured such that the relatively solid structure formed after pulling the tether taut is a helix. The members are desirably no wider than 20 mm. Each of the non-inflatable members may comprise a spherical body having an opening on one side centered about a radial axis and leading to an internal cavity, and a nipple projecting from another side. The cavity may be stepped and narrows into an internal through bore that angles within the spherical body and continues outward through the nipple along a different radial axis, the nipple being stepped to fit within a stepped cavity of another of the members. Preferably, the axes aligned with the cavity and nipple define an obtuse included angle of between about 120-150°. Each cavity may have a helical ledge that terminates in a small notch, while the nipple has a single protrusion along its length, such that when a nipple is introduced into a cavity and forced together, the members will rotate until the protrusion on the nipple seats in the notch. In one embodiment, the rotational orientation of any one member relative to another is unrestricted, while in another each member may only join together in a particular rotational orientation with another member.

In accordance with a still further embodiment, a passive intragastric obesity treatment implant has an expandable net-like body formed of a plurality of struts. The body has a relaxed configuration with a size sufficient to contact the interior stomach walls upon contraction thereof, the body including a generally tubular outer portion connected to two invertible end portions terminating in cups, one of the cups including structure for mating with a delivery tube, and the other cup being solid. The relaxed diameter of the body is preferably slightly larger than the average obese patient's upper stomach interior, and larger than the lower stomach. The relaxed shape of the body may define an outer cylindrical periphery and an hourglass-shaped inner profile. Desirably, the cups are shaped similarly to nest together in the center of the structure.

Another passive intragastric obesity treatment implant disclosed herein comprises a non-inflated stent having a relaxed configuration that forms a truncated cone with one end larger than the other. The conical stent has a size that conforms to the stomach of an adult patient so as to contact the interior stomach walls in the region of the greater and lesser curvatures, but has an axial dimension that prevents stimulation of the pylorus and cardia regions, the stent comprising wires covered with a silicone sleeve.

Another passive intragastric obesity treatment implant of the present application features an elongated solid member having a relaxed configuration that forms a coil, opposite free ends of the coil being adapted to connect together to form a continuous loop. The coil assumes a three-dimensional shape upon implant in the stomach having a size that generally fits within the stomach of an adult patient so as to contact the interior stomach walls upon contraction thereof. The implant further may include a plurality of necked-down sections along the length of the elongated member providing areas for cutting the elongated member. The elongated member preferably has a distal end connector with a lumen, and a proximal end connector with a lumen and a side aperture spaced from the proximal end connector. The implant further may include a tether that extends through the hollow lumen on the distal end connector and is secured therein, and passes in through the proximal end connector lumen and outward through the side aperture, the proximal and distal end connectors being brought together upon pulling the tether taut.

The present invention also includes a intragastric device for the treatment of obesity, the device comprising an elongated member having a relaxed configuration that forms a non-uniform diameter helix, with a middle coil of the helix having a maximum diameter, and at least one end coil of the helix having a diameter which is less than the diameter of the middle coil, the relaxed configuration of the elongated member having a length and a maximum diameter such that the device can be placed in and fit within the stomach of a patient so that the device once implanted in the stomach of the patient span or occupies along at least one axis the distance or span between the antrum and cardia walls of the stomach and thereat make contact with and apply a pressure to the stomach walls, the elongated member being formed of a material which permits it to be stretched into a substantially linear delivery configuration and wherein the device can substantially resist degradation over a period of at least six months while the device is implanted in the stomach. To substantially resist degradation means that when placed in the acid environment of the stomach the device still functions at least substantially as intended, that is a clinically significant result (i.e. weight loss or the maintenance of a weight loss) can still be obtained.

A further understanding of the nature and advantages of the invention will become apparent by reference to the remaining portions of the specification and drawings.

BRIEF DESCRIPTION OF THE DRAWINGS

Features and advantages of the present invention will become appreciated as the same become better understood with reference to the specification, claims, and appended drawings wherein:

FIG. 1 is a sectional view through a human stomach illustrating a spiral-shaped intragastric obesity treatment device described herein;

FIG. 2 is an elevational view of the obesity treatment device of FIG. 1, and FIG. 2A is a sectional view therethrough;

FIG. 3 is an elevational view of an alternative spiral-shaped intragastric obesity treatment device of the present application;

FIG. 8 is a perspective view of a still further intragastric obesity treatment device of the present application including a net-like expandable stent;

FIGS. 9A and 9B are schematic illustrations of the shape of the net-like expandable stent in expanded and contracted configurations;

FIGS. 10A and 10B are enlarged perspective views of mating cups used to expand and contract the device of FIG. 8;

FIG. 12 is a perspective view of a coiled solid intragastric obesity treatment device, while

DETAILED DESCRIPTION OF THE PREFERRED EMBODIMENTS

Figure 4:
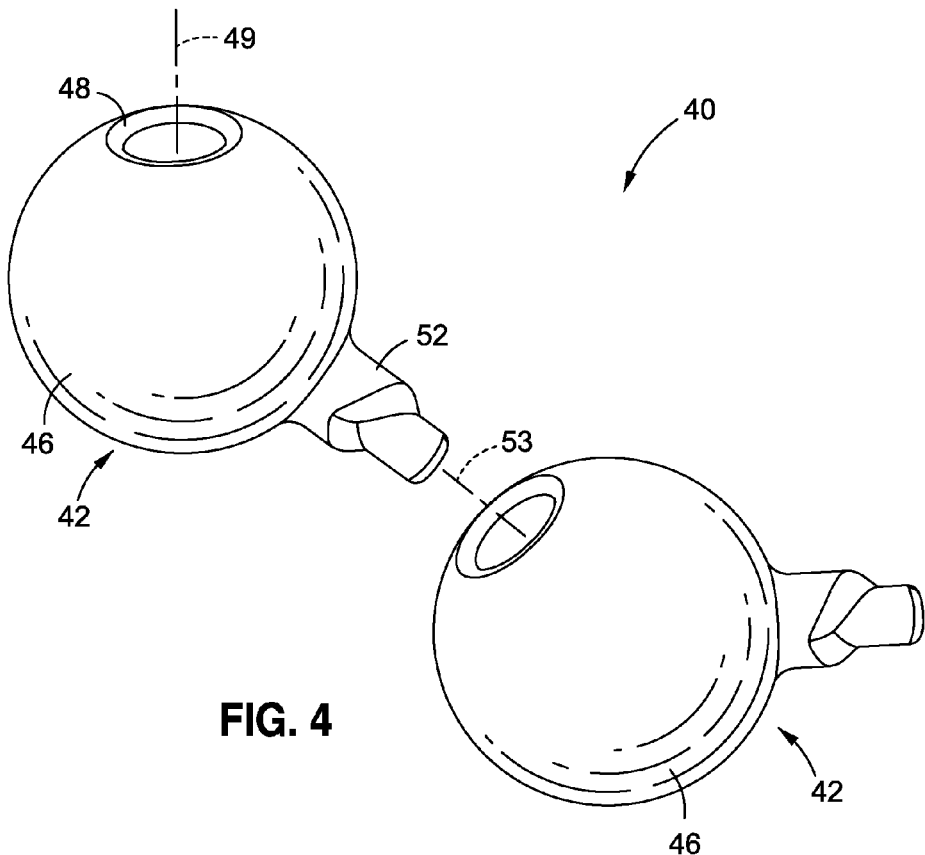
FIG. 4 is an exploded perspective view of two space-occupying members that mate to form an intragastric obesity treatment device.

The present invention is directed to a variety of different intragastric devices that passively treat obesity by taking up space within the stomach or contact areas in and around the stomach to induce feelings of satiety. Furthermore, some devices described herein affect the rate of stomach emptying. It should be understood that a number of the disclosed devices provide more than one of these passive aspects, and also that any disclosed structure could be combined with another disclosed structure unless physically impossible. As such, combinations of the passive satiety-inducing features disclosed herein, even if not explicitly stated, are contemplated. The term "passive" refers primarily to a lack of any moving parts within the devices, but in general to the inert nature of the various devices. A passive device as defined herein, however, is not one that cannot affect change or stimulate the stomach, but rather one that may do so without any physical or chemical changes to its basic makeup.

FIG. 1 illustrates a first space-occupying device 20, but also illustrates the anatomy of the human stomach, which will be described first. The major function of the stomach is to temporarily store food and release it slowly into the duodenum. The esophagus extending downward from the mouth connects to the stomach via esophageal sphincter, which regulates flow food into the stomach cavity. The cardia surrounds the superior opening of the stomach. The rounded portion superior to the body and adjacent the cardia is the fundus. Inferior to the fundus is the large central portion of the stomach, called the body, that is lined with muscles that contract and relax repetitively to churn the food therein. The stomach processes the food to a semi-solid "chyme," which enables better contact with the mucous membrane of the intestines, thereby facilitating absorption of nutrients. In addition, the stomach is an important site of enzyme production.

Lower down in the stomach the antrum connects the body to the pylorus, which leads into the duodenum. Below the stomach, the duodenum leads into the upper part of the small intestine (not shown); the jejunum makes up about one-third of the small intestine. The region of the stomach that connects to the duodenum is the pylorus. The pylorus communicates with the duodenum of the small intestine via the pyloric sphincter (valve). This valve regulates the passage of chyme from stomach to duodenum and it prevents backflow of chyme from duodenum to stomach.

A first category of passive satiety-inducing devices of the present application function similar to existing intragastric balloons in that they take up space within the stomach. For example, the space-occupying device 20 of FIGS. 1-2A is configured as a large diameter, plastic helical spring that may be straightened and fed down into the stomach, through the esophagus, by way of a pre-inserted, thin-walled plastic tube (not shown). The insertion tube temporarily holds the device in a straightened configuration. The inherent spring force in the device 20 after placement permits it to resume its relaxed helical configuration within the stomach cavity. The elongated spring device 20 thus applies pressure between the antrum and cardia, which force on the cardia triggers release of satiety-inducing hormones, so meal time is likely to be shortened.

The coil-like device 20 is intended to be a single use implant placed in the stomach transorally without invasive surgery, and recovery time is believed to be minimal. The device may be left in place one year or longer, which is somewhat material-dependent in the acidic stomach environment.

As seen best in FIG. 2, the spring device 20 in a relaxed state has a superior end 22a and an inferior end 22b, and the helix gradually tapers larger toward a midsection. The helix defined by the coil is somewhat offset so as to have a maximum diameter coil 24 closer to the superior end 22a. The asymmetric helix of the device 20 thus better conforms to the approximate shape of the stomach cavity, as seen in FIG. 1. Also, the opposite ends 22a, 22b of this device are slightly bent back away from the stomach walls, so no "sharp" points are presented that might apply irritating pressure to stomach walls. Instead, forces are exerted relatively evenly along the side surfaces, and at the superior and inferior coils of the spring 20.

The entire spring/tube 20 may be hollow, as seen in FIG. 2A. The device 20 may be formed first as a standard tube, and then post-cured around a mandrel, to assume and retain its helical spring-like relaxed shape. The ends shall be sealed to prevent ingress of fluids in the stomach environment.

Alternatively, the spring device 20 could be made with a thin metal wire as a core covered with a soft outer layer, such as Teflon.

An alternative spring device 30 shown in FIG. 3 is configured so that the "spring" has its smallest diameter in the center region 32, while remaining larger at the ends 34a, 34b. Indeed, the center region 32 preferably extends relatively straight without coils which minimizes any structural impediment to the grinding action of the body portion of the stomach. The top end 34a is desirably larger than the bottom end 34b, as in the first embodiment.

For device insertion and removal, a lubricated, Teflon or similar material, thin-walled tube would be inserted down the esophagus, and partially into the stomach. The spring device 20 or 30 would be stressed and straightened as it is introduced and guided down the tube. As the device exits the tube, into the stomach, it would quickly return to its as-molded, spring-like shape. A tab (shown at 26 in FIG. 2) could be melt-molded into the upper end when the ends are sealed to serve as a grasping point for device removal, back up the tube.

Another space-occupying device 40 is shown in FIGS. 4-7, and comprises a plurality of rounded sequential members 42 such as balls linked in series and adapted to assume a particular shape when pulled taut. The device 40 exists in two states—an "unassembled state" for device implantation/removal, and an "assembled state" which configures the device in a specific orientation after implantation while in the stomach. The device 40 is intended to be located completely within the stomach compartment. At the conclusion of treatment, the device is retrieved gastroendoscopically. This device may induce weight loss by taking up space within the stomach to reduce the total quantity of food ingested during a meal and reduce the sensation of preprandial hunger while implanted. Also, the shape of the assembled device 40 encourages stimulation of the stomach walls, which through mechanical transduction will trigger the efferent nerves in the stomach so as to encourage satiety.

Figures 6A, 6B:
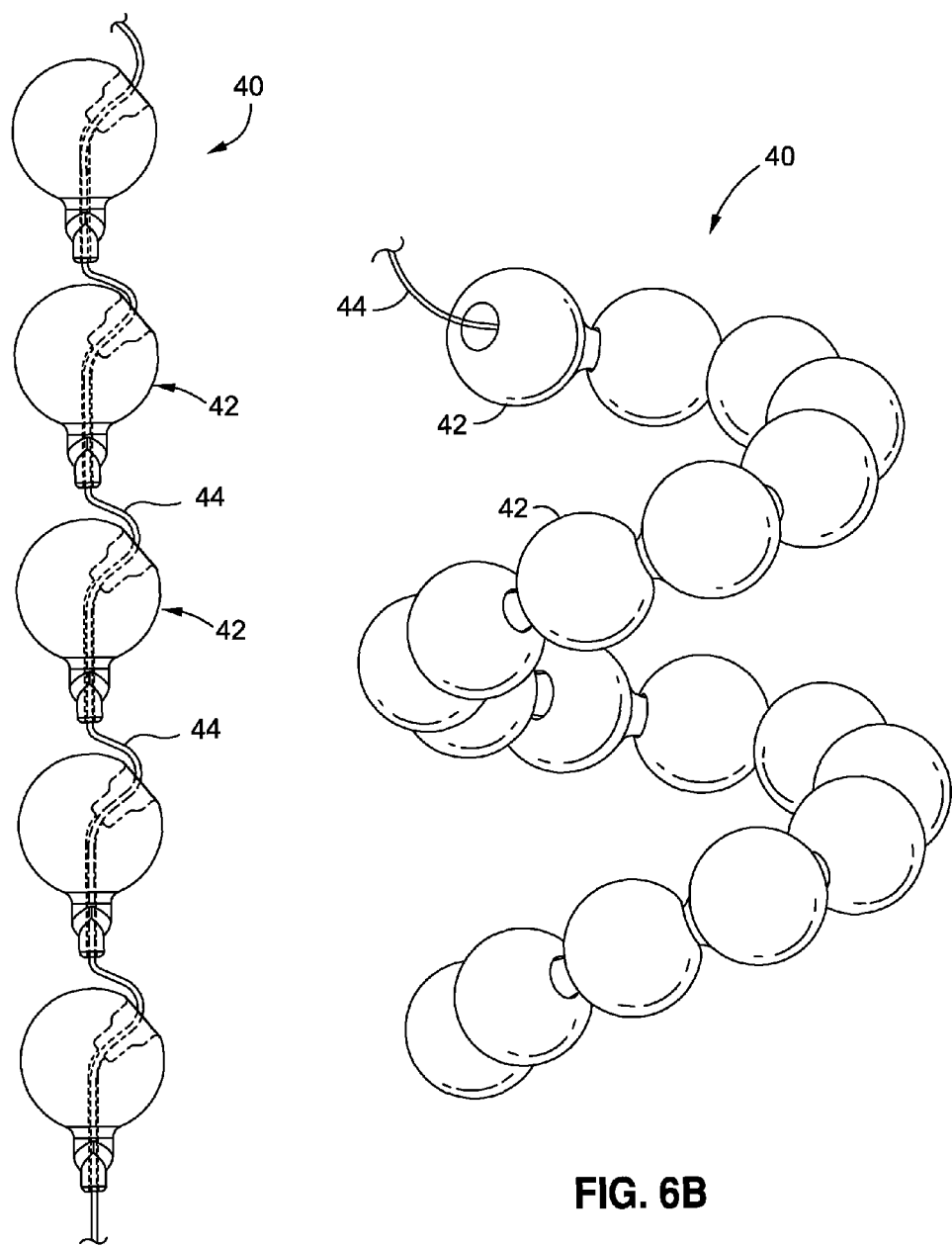
FIG. 6A is a perspective view of an assembly of the space-occupying members of FIG. 4 joined by a tether in a loose configuration.
FIG. 6B is a perspective view of the assembly of space-occupying members of FIG. 6A after the tether has been pulled taut to cause the members to mate and form a predetermined shape.

As seen best in FIGS. 6A and 6B, the device 40 comprises a series of individual members 42 strung together onto a single tether 44. Each individual member 42 is sized such that it can be easily implanted and removed through the esophagus (no wider than 20 mm).

Figure 4A:
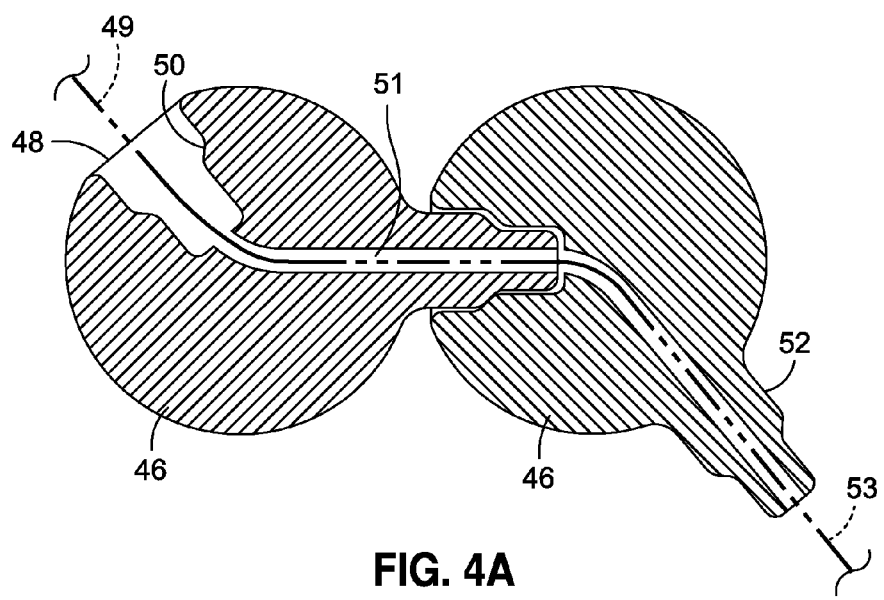
FIG. 4A is a sectional view through the members after mating.

In one embodiment, and with reference to FIGS. 4 and 4A, each member 42 comprises a spherical body 46 having an opening 48 on one side centered about an axis 49 and leading to an internal stepped cavity 50. The cavity 50 narrows into an internal through bore 51 that angles within the spherical body 46 and continues outward through a stepped nipple 52 projecting from another side of the spherical body along an axis 53. The axes 49 and 53 define an obtuse included angle, preferably between about 120-150°. The stepped nipple 52 of one member 42 fits closely within the stepped cavity 50 of another, as seen in FIG. 4A. The rotational orientation of any one stepped nipple 52 within another cavity 50 may be unrestricted, or the members 42 may join together in a particular orientation, such as with the use of a notch 54 on the nipple 52 shown in FIG. 4 that mates with a similar projection (not shown) within the cavity 50 of the adjacent member.

Figure 5:
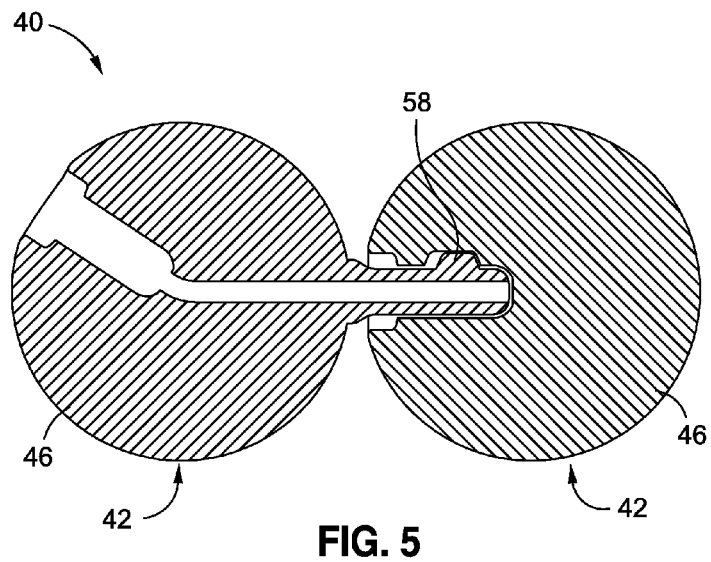
FIG. 5 is a sectional view through two alternative space-occupying members similar to those in FIG. 4.
Figure 5A:
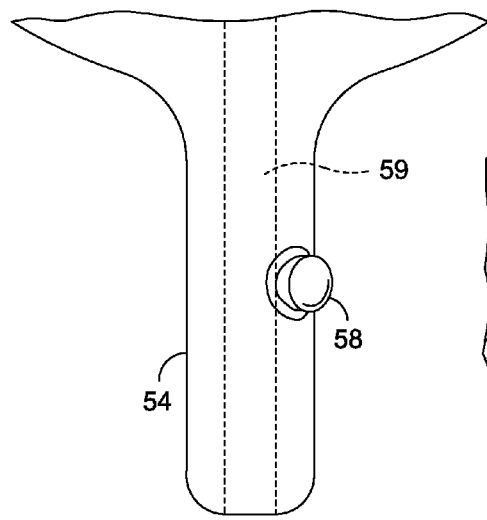
FIGS. 5A and 5B are enlarged views of the mating components of the alternative space-occupying members of FIG. 5.
Figure 5B:
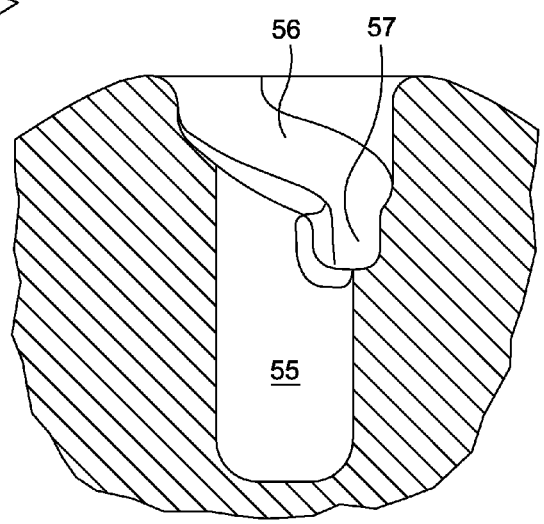

In a preferred embodiment, as seen in FIGS. 5-5B, the sequential members 42 incorporate features which allow them to mate with each other in a specific orientation. For example, each member 42 features a male post 54 and female cavity 55. The female cavity 55 has a helical ledge 56 inside of it which terminates in a small notch 57, while the male post has a single protrusion 58 along its length. The design of these two features is such that if a post 54 is introduced into a cavity 55 and forced together, the members 42 will rotate until the protrusion 58 on the post seats itself in the notch 57. The ledge 56 consists of a half turn helix, mirrored across the part; that is, there are two half-turn helices commencing at locations spaced 180° around the cavity 55 but both terminating in the notch 57. This ensures that even if misaligned 180° initially, the male post 54 will rotate in one direction or the other to seat itself in the cavity 55.

The post 54 and cavity 55 on each sequential member 42 will be connected through a single lumen 59 running through each member to form a series of sequential lumens. This will allow each member 42 to be threaded onto a tether 44 as shown below. If assembled onto the tether 44 loosely, as seen in FIG. 6A, the individual members 42 will be allowed to move freely relative to one another, facilitating implantation and removal. On the other hand, if the tether 44 is pulled taut, as seen in FIG. 6B, the sequential members 42 will automatically assemble themselves according to the features described above into a single, predictable, fairly rigid device 40. To facilitate assembly, each of the cavities 55 features a lead-in taper to help guide the adjacent post 54 therein.

The specific embodiment of FIG. 6B illustrates a helical shape to the assembled device 40. If the parameters of the current design are manipulated, the compactness of the helix (its pitch and diameter) may be altered. The formation of numerous other shapes through the use of different individual components is also contemplated. For example, the helical shape shown in FIG. 6B may be formed by connecting a series of identically-shaped and oriented members 42 in a pattern that can be symbolized as AAAA . . . , etc. Consider alternating two different components into an A-B-A-B pattern, such that the relative angle between the members 42 alternates between adjacent members, for example. A huge number of permutations can be envisioned with various component designs (A, B, C, etc.) and various patterns (AAAABBBB, ABAB, ABBA, ABCABC, etc.). Additionally, this embodiment utilizes a single tether 44 running through all of the members 42. It is also possible to envision a device which utilizes a main tether, with secondary (or even tertiary and beyond) tethers branching off from it. This increases the number of embodiments further.

Figure 7A:
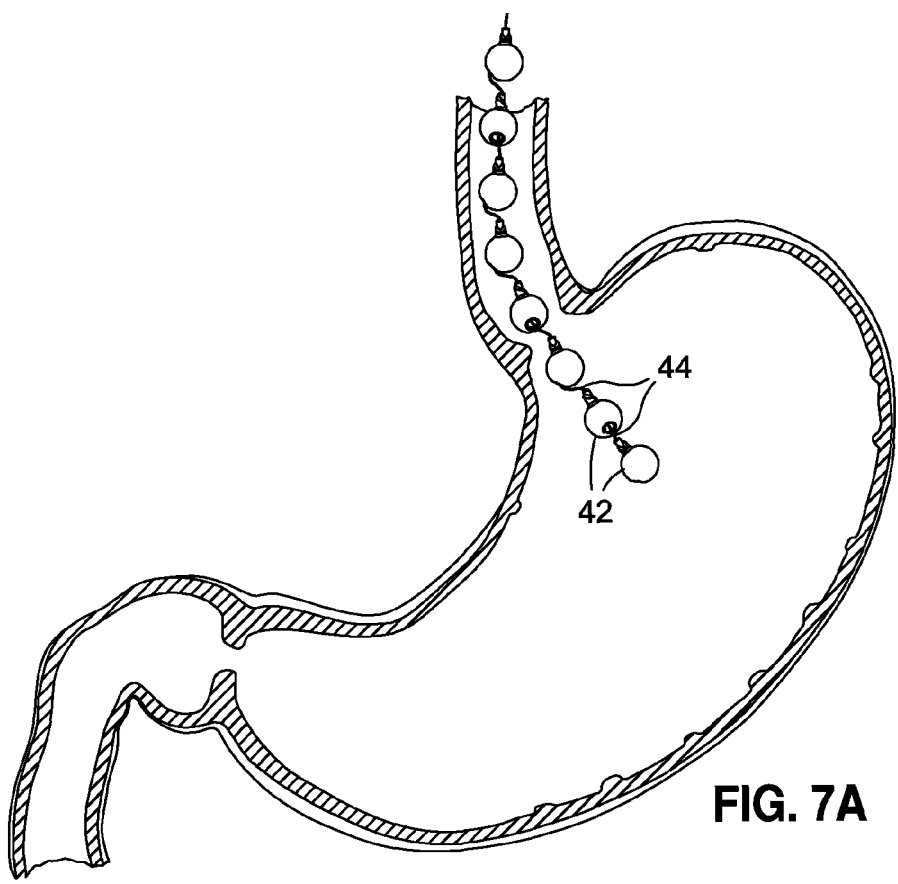
FIGS. 7A and 7B illustrate delivery to the stomach cavity of the assembly of space-occupying members shown in FIGS. 6A and 6B and conversion to the predetermined shape.
Figure 7B:
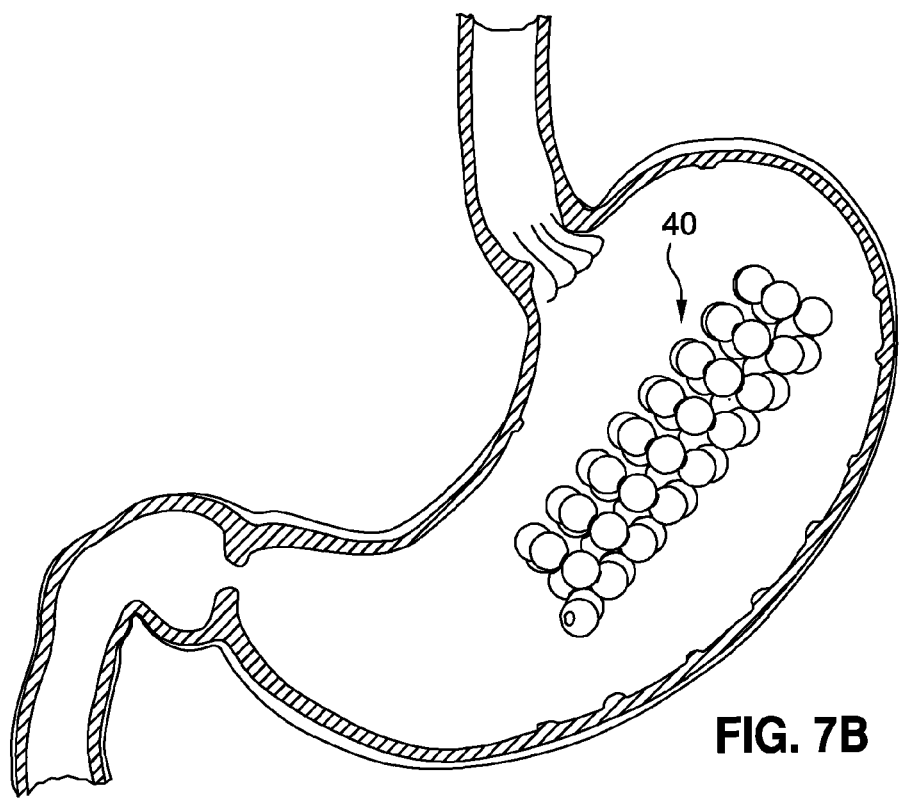

FIGS. 7A and 7B show the device relative to a stomach model, both for insertion/removal and while in the stomach. During insertion, as seen in FIG. 7A, the sequential members 42 connected by the tether 44 are advanced transorally and through the esophagus into the stomach cavity. Once again, the members 42 are sized small enough to fit through the esophagus without trouble, and are preferably spherical in shape to facilitate advancing through the esophagus. Once within the stomach cavity, as seen in FIG. 7B, the operator pulls the tether 44 taut to form the assembled device 40. The tether 44 may be secured to the distalmost member 42, and anchored to the proximal member after being pulled taut. The extra length of the tether is then severed.

As previously mentioned, one area in which satiety can be induced is stimulating the upper reaches of the stomach, in particular the cardia.

An exemplary cardia-stimulating device 140 is seen in FIG. 8, and comprises an expandable intragastric stent. The expandable intragastric stent 140 controls the amount of food allowed to pass through the esophagus and into the stomach. Ingestion is accordingly restricted primarily by stimulating stomach nerves which are responsible for triggering release of hormones that induce feelings of satiety.

Such neurostimulation would be continuous, so it is thought that appetite suppression will also be continuous.

It has been shown that the upper portion of the stomach is most sensitive to such neurostimulation. For this reason the intragastric stent 140 is sized to migrate toward the upper stomach area in this way: Fully deployed diameter is in the 2½ inch (6.4 cm) range, slightly larger than the average obese patient's upper stomach interior, but considerably larger than the lower stomach. On this basis, the device should tend to gravitate toward the larger, upper stomach region.

The intragastric stent 140 comprises a net-like structure 142 having a plurality of interconnected wires that define an outer cylindrical periphery and a somewhat hourglass-shaped inner profile when expanded. FIGS. 9A and 9B schematically show the net-like structure 142 in its expanded and radially contracted configurations, respectively. Opposite ends of the net-like structure 142 are joined together at cups 144, 146 which, in the expanded state, nest together in the center of the structure. In the contracted state or FIG. 9B, which is axially elongated, the cups 144, 146 are separated at each end of the structure.

The intragastric stent 140 is configured to be placed inside the patient's stomach and acts to control the amount of food allowed to pass through the esophagus and into the stomach by stimulating stomach nerves, such as the vagal or splanctic, by exerting pressure on the inside walls of the stomach. In particular, the intragastric stent 140 may be sized at approximately 2.5 inches (6.4 cm) in diameter when expanded to enhance migration towards the upper stomach since this portion of the stomach is the most sensitive to neurostimulation. By pressuring the inside walls, and stimulating the stomach nerves, appetite suppressing hormones may be released naturally by the patient's body and thereby promoting the feeling of satiety in the patient.

Intragastric stent 140 may be inserted into the patient's stomach by using an obturator 148. The obturator 148 comprises an elongated flexible plastic tube having a distal end that flares outward in two apposing, outwardly facing tabs or wings 150 which are radio-opaque. A stiff wire 152 slides within the obturator 148. As shown in FIG. 10B, the wings 150 may be configured to slide and "snap" into openings or slots 154 of the first cup 146 and hold the obturator 148 in place.

FIG. 10A illustrates another view of the obturator 148 in close proximity to the two cups (in nested state). The internal wire 152 protrudes through the proximal end of the obturator 148. When the obturator 148 is held in place against the first cup 146 by the wings 150, the wire 152 may extend through a hole 156 in the first cup 146 and contact the second cup 144. The second, stacked outer cup 144 has no bottom hole, so the wire 152 passing through the hole 156 in the first cup 146 bears against the bottom inside of the second cup and moves it away from the first cup to achieve a non-nested state as shown schematically in FIG. 9B. This action causes the stent-like wiring attached to the first cup 146 and second cup 144 to invert and elongate, allowing the compressed intragastric stent 140 to be moved down the patient's mouth and esophagus, into the patient's stomach. Upon reaching the destination, withdrawing the wire 152 from the distal end of the plastic tube permits the two cups 144, 146 to be drawn toward one another via spring action from the compressed net 142. In so doing, the stent expands to its fully open, natural state, while inside the stomach. The distal end of the obturator protrudes out the mouth during device insertion.

For device removal, a radiographic camera is employed to monitor the procedure. The flexible obturator 148 is re-inserted through the esophagus and engages the first cup 146, which has been suspended in the approximate center of the stomach. The twin wings 150 on the tube 148 are radiographically guided to engage the slots 154 in the first cup. Then the wire is re-inserted through the tube's distal end, as far as it goes, without exerting excessive force. Then, the inner wire is pushed through the hole 156 in the bottom of the first cup 146 and guided into the bottom of the second cup 144. Since there is no hole in the second cup for the wire to pass through as in the first cup, the wire is made to bear against the bottom of the second cup. Pushing the wire further down the plastic tube (while holding the tube from ingressing any further), the wire is employed to spread the cups apart to achieve the non-nested state, inversion of the inner walls of the intragastric stent 140 and substantially elongation is achieved. Accordingly, by holding the intragastric stent 140 in this state, the intragastric stent 140 may be easily removed without discomfort.

In one aspect, Nitinol shape memory wire may be utilized to fabricate the compressible stent-like configuration. In another aspect, the cups may be constructed out of metal or other acidic-resisting materials. The ingestion net may be spot welded at every intersection where the wires cross or touch, and further may be welded to the cups themselves.

In an alternative embodiment, a thin, stainless steel tube with a diameter of 2.5 inches may be used in place of the Nitinol shape memory wire. In this embodiment, the tube may be laser-machined into a compressible stent-like configuration similar to the configuration shown in FIG. 8. Wires may then be welded to the ends of the tube and then welded to metal cups (similar to the cups shown in FIG. 8). Functionally, the tube version of the intragastric stent 140 may operate in a very similar fashion as the embodiment described above, compressing when the obturator and wire are used, and returning to its non-compressed state when the obturator and wire are removed.

A third embodiment of the intragastric stent design (not shown) is similar in most respects, except that instead of a full net-like configuration of wire, welded at all the intersecting points, longitudinal wires only would be used. In this version welding is only required at the distal and proximal ends, to hold identical pre-curved wires in assembly. Also, the obturator would lock onto the proximal end in a similar fashion as the other versions, but the central wire would pass through the welded proximal end and push on the welded distal end, thereby holding the device in a collapsed state for insertion and removal. This version would need no cups near the geometric center.

Figure 11A:
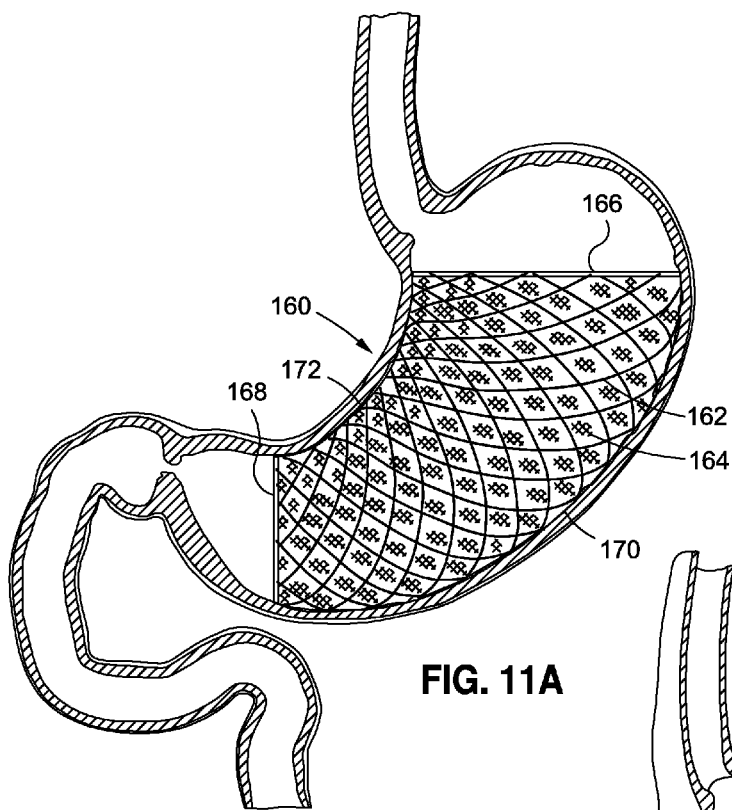
FIGS. 11A-11C are several different views of an exemplary stomach-conforming sleeve that stimulates the lesser and greater curvatures of the stomach.
Figure 11B:
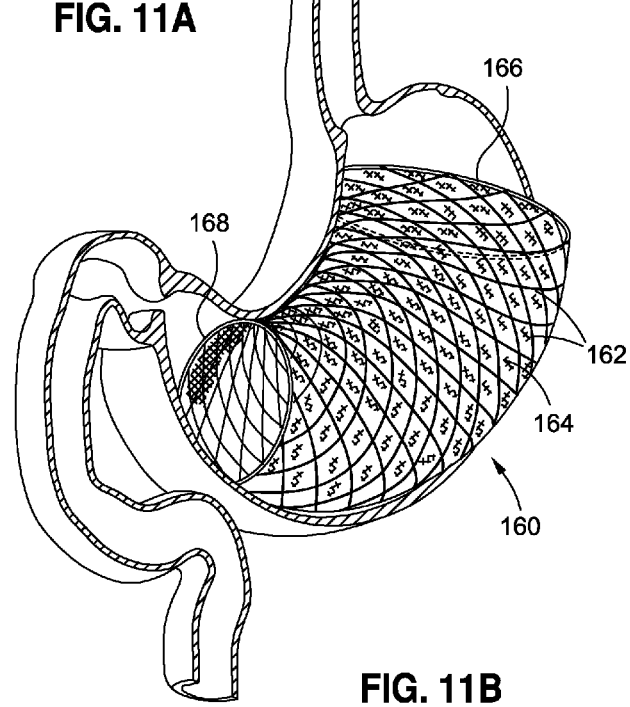
Figure 11C:
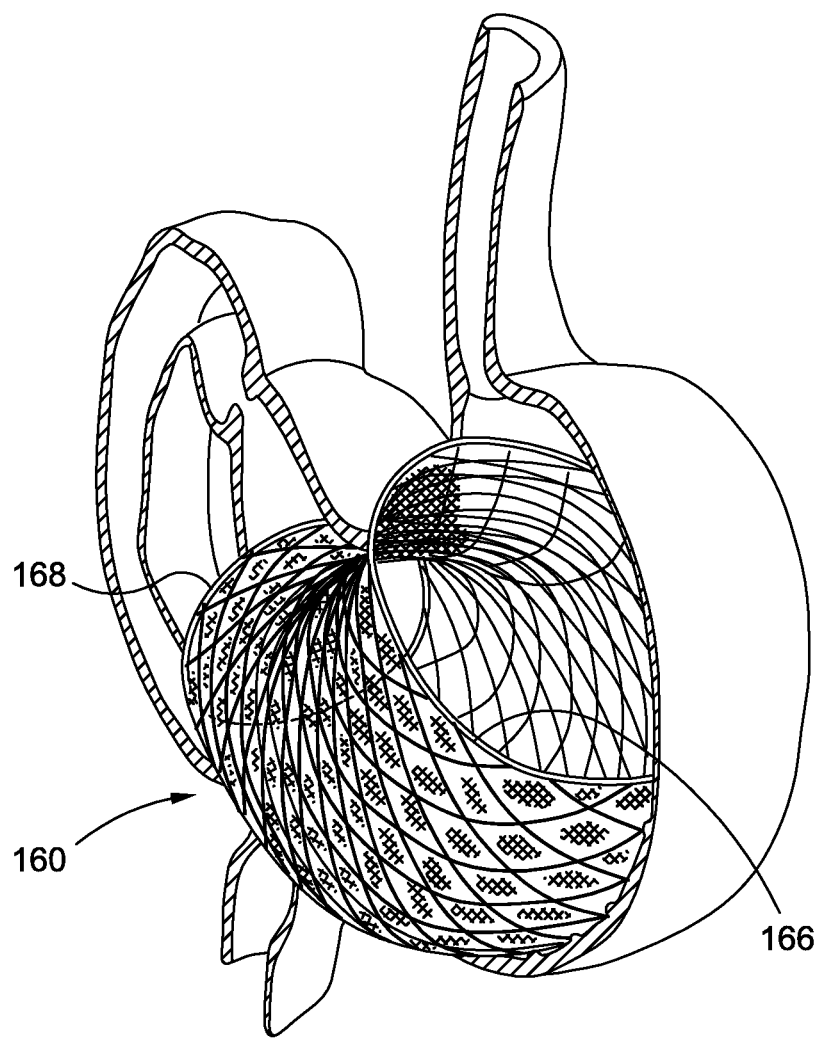

FIGS. 11A-11C are several different views of an exemplary stomach-conforming resilient stent 160 that stimulates the lesser and greater curvatures of the stomach. The stent 160 preferably comprises a latticework of wires 162 defining the shape of the stent and a flexible sleeve 164 extending the full length of the stent and spanning the spaces between the wires 162. In one embodiment, the wires 162 are made of Nitinol and the sleeve 164 is silicone. In another embodiment, the wires 162 themselves may be coated in silicone and then the sleeve 164 secured thereto, either within or without.

The stent 160 defines a generally truncated horn shape that conforms to a mid-portion of the stomach, and includes a relatively larger inflow rim 166 and a smaller outflow rim 168. Although not shown, the relaxed shape of the resilient stent 160 has substantially the same shape, which approximates a truncated arcuate cone. As such, the stent 160 is desirably symmetrical about a midplane coinciding with the sectional plane in FIG. 11A. A lower generatrix 170 along the plane of symmetry through the stent 160 thus has a larger radius and larger chordal distance between the inflow and outflow rims 166, 168 than an upper generatrix 172 through the stent, the former conforming to the greater curvature of the stomach and the latter to the lesser curvature. However, the stent 116 in its relaxed shape may alternatively be provided as a truncated cone, which expands outward and conforms to the stomach nonetheless, though not in the same manner as shown. In a preferred embodiment, the stent 160 in its relaxed state has a diameter of up to about 20 cm. Of course, when implanted the stent 160 conforms to the stomach and the diameter of the inflow rim 166 will be greater than the diameter of the outflow rim 168. Furthermore, in the implanted configuration shown, the chordal length of the lower generatrix 170 is desirably up to about 60 cm, while the chordal length of the upper generatrix 172 is less since it conforms to the lesser curvature but potentially up to about 60 cm.

The stent 160 desirably does not stimulate the fundus or pylorus, or reach up to the cardia region. Instead the stent 160 only presses against the lesser and greater curvatures of the stomach. The stent 160 applies an outward pressure against the greater or lesser curvatures of the stomach to help induce the sensation of satiety. At the same time, because of their relatively large lumen defined within, the stent 160 permits uninhibited passage of food through the stomach, and transfers substantially all of the churning force of the stomach to the food.

Ribs, barbs, struts, or other such outward members may be provided to prevent unintentional rotation or migration of the stent within the stomach after implant. In a preferred embodiment, the inflow rim 166 will have features (not shown) for delivery and removal. For example, grasping tabs which extended proximally from the rim 166 may be provided. Alternatively, one or more suture loops extending proximally from the rim 166 may be provided for grasping to collapse the stent 160 into a removal tube (not shown). Finally, the wire elements 162 of the stent 160 are desirably radiopaque to help clinicians diagnose patient outcomes.

Figure 12:
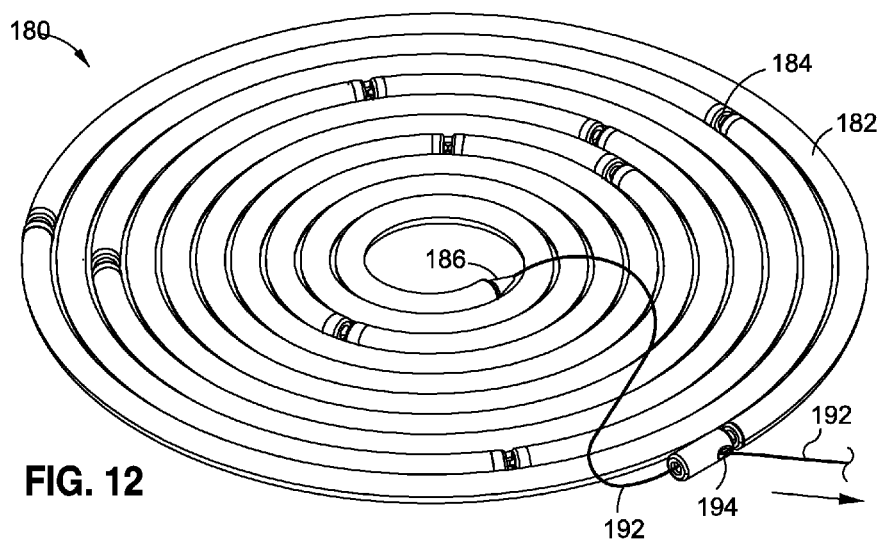
Figure 12A:
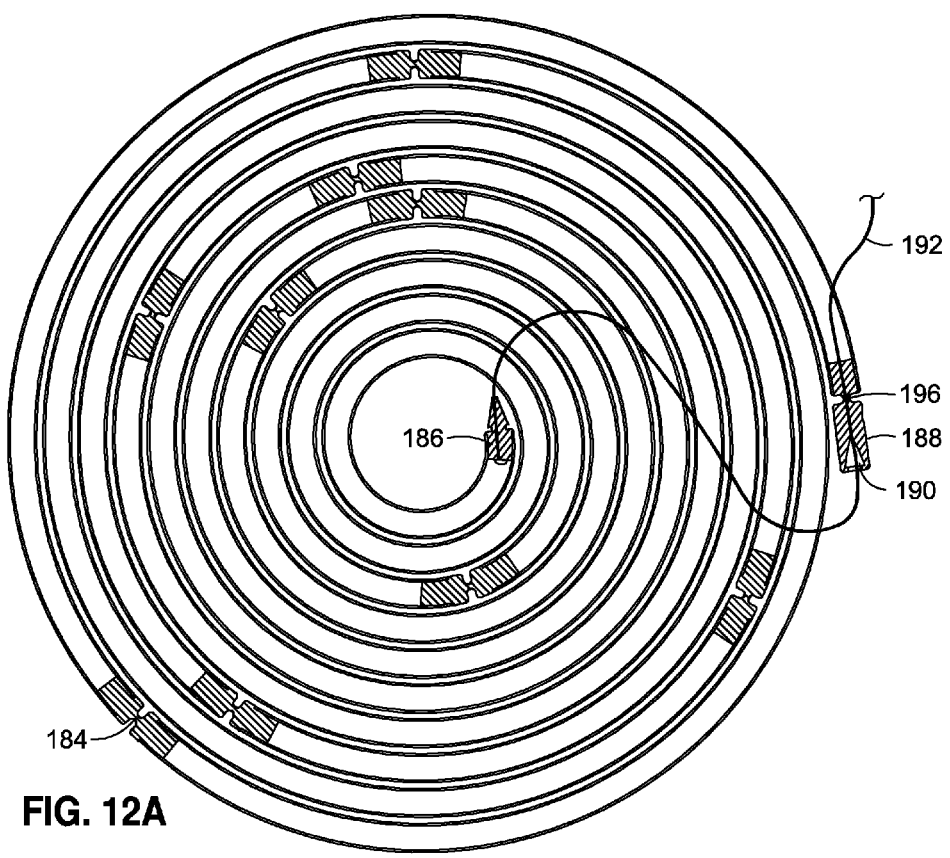
FIG. 12A is a longitudinal sectional view thereof.
Figure 12B:
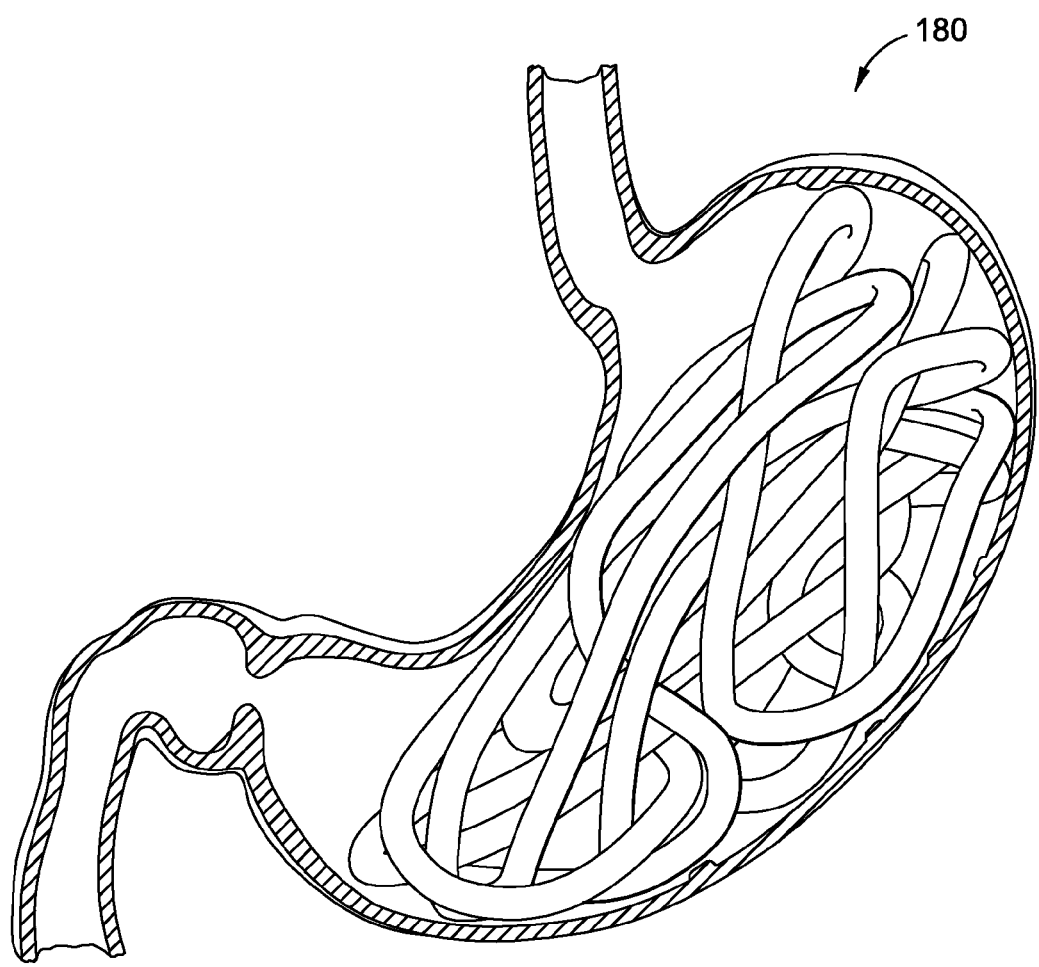
FIG. 12B is a sectional view through the stomach showing the device of FIG. 12 after deployment and connection of its two free ends showing an exemplary three-dimensional configuration.

A still further satiety-inducing device 180 of the present application is seen in FIGS. 12 and 12A-12B, and includes a solid member 182 that is arranged in a spiral when at rest, or prior to use. The device 180 is configured as a long, snake-like object that may be straightened and fed down into the stomach, through the esophagus, wherein the two free ends are connected to form the three-dimensional beehive shaped shown in FIG. 12B. The assembled device 180 thus occupies space in the stomach, so the amount of food normally ingested is restricted since the usable stomach volume is reduced. This device requires no saline inflation, but occupies approximately the same volume (400 ml) as the aforementioned Orbera® System, which is proven to occupy a sufficient amount of space to facilitate weight loss. Eliminating the need for inflation greatly simplifies the implantation and removal. In addition to taking up space in the stomach, pressure exerted on the stomach walls is known to effect nerves, causing early feelings of satiety. Pressure points will vary as device migrates around with normally variable stomach contractions.

The device 180 comprises an elongated tubular member 182 formed of a suitable polymer and having a hollow through bore. Tubular member 182 in the illustrated embodiment is made up of a series of shorter members connected at neck regions 184. A distal end includes a tapered tip 186 which may be a plug, as seen in FIG. 12A. A proximal end features a cylindrical tip 188 having a conical cavity 190. The cavity 190 is shaped to receive the tapered tip 186 and lock it therein, such as with the use of a barb and overhanging lip. This connection prevents separation of the ends in the absence of excessive force.

In order to prevent the ends of this snake-like device from passing into the intestines through the pylorus and thereby causing obstruction, a special string, wire, or tethering line 192 of some kind remains outside the body during insertion, ingressing through the mouth. The tether 192 attaches to the distal end of the device 180, such as shown in the sectional view of FIG. 12A, and extends through a bore in the cylindrical tip 188 at the proximal end and out a side port 194 therein, as seen in FIG. 12. The two ends may be directed together by pulling the tether 192, and are configured to "snap" together, forming a non-ending loop, such as in the tangled shape seen in FIG. 12B. The size of the loop, when presented to the opening of the pylorus, is too large and stiff to pass through the orifice, and therefore cannot pass into the jejunum. In this way, the device will not cause intestinal obstruction or need for immediate surgical intervention. Although the device 180 may become tangled such that the two free ends are difficult to locate, the presence of multiple neck regions 184 provides a number of locations at which the device can be severed, thus facilitating removal.

A necked-down area 196 near the proximal end can be temporarily held by a standard grabber, inserted transorally, to resist the force of pulling on the string to facilitate end-to-end connection. For device removal, the same necked-down area 196 can be cut through, using a standard, transorally inserted cutter. Then a standard grabber can be used to pull the device back through the esophagus and out the mouth. These areas preferably have a radio-opaque additive so they may be seen with X-ray during removal procedure.

The multiple necked-down areas 184 may be easily cut through, thus providing additional "cutting sites" spaced over the length of the device, and to facilitate removal in pieces, to avoid or remedy tangling that may already have occurred.

An alternative embodiment (not shown) could include springs inside the identical tube lengths, to overcome the natural tendency of the plastic tube material to acquire a set, therefore fixing the device in a non-pressure-exerting condition.

In one aspect, the artificial coil-like satiety-inducing device 180 may be constructed out of polypropylene or other suitable materials for resisting the acidity of the stomach environment. In another aspect, the artificial coil-like device 180 may take up a volume of at least 400 cubic centimeters (cc) when inserted into the patient's stomach.

It should also be stated that any of the embodiments described herein may utilize materials that improve the efficacy of the device. For example, a number of elastomeric materials may be used including, but not limited to, rubbers, fluorosilicones, fluoroelastomers, thermoplastic elastomers, or any combinations thereof. The materials are desirably selected so as to increase the durability of the device and facilitate implantation of at least six months, and preferably more than 1 year.

Material selection may also improve the safety of the device. Some of the materials suggested herein, for example, may allow for a thinner wall thickness and have a lower coefficient of friction than the current device which may aid in the natural passage of the balloon through the GI tract should the device spontaneously deflate.

The implantable devices described herein will be subjected to clinical testing in humans. The devices are intended to treat obesity, which is variously defined by different medical authorities. In general, the terms "overweight" and "obese" are labels for ranges of weight that are greater than what is generally considered healthy for a given height. The terms also identify ranges of weight that have been shown to increase the likelihood of certain diseases and other health problems. Applicants propose implanting the devices as described herein into a clinical survey group of obese patients in order to monitor weight loss.

The clinical studies will utilize the devices described above in conjunction with the following parameters.

Materials:

a. Silicone materials used include 3206 silicone for any shells, inflatable structures, or otherwise flexible hollow structures. Any fill valves will be made from 4850 silicone with 6% $BaSo_4$. Tubular structures or other flexible conduits will be made from silicone rubber as defined by the Food and Drug Administration (FDA) in the Code of Federal Regulations (CFR) Title 21 Section 177.2600.

Purposes:

i. the devices are for human implant, ii. the devices are intended to occupy gastric space while also applying intermittent pressure to various and continually changing areas of the stomach;

iii. the devices are intended to stimulate feelings of satiety, thereby functioning as a treatment for obesity.

General Implant Procedures:

i. The device is intended to be implanted transorally via endoscope into the corpus of the stomach.

ii. Implantation of the medical devices will occur via endoscopy.

iii. Nasal/Respiratory administration of oxygen and isoflurane to be used during surgical procedures to maintain anesthesia as necessary.

One exemplary implant procedure is listed below.

i. Perform preliminary endoscopy on the patient to examine the GI tract and determine if there are any anatomical anomalies which may affect the procedure and/or outcome of the study.

ii. Insert and introducer into the over-tube.

iii. Insert a gastroscope through the introducer inlet until the flexible portion of the gastroscope is fully exited the distal end of the introducer.

iv. Leading under endoscopic vision, gently navigate the gastroscope, followed by the introducer/over-tube, into the stomach.

v. Remove gastroscope and introducer while keeping the over-tube in place.

vi. OPTIONAL: Place the insufflation cap on the over-tubes inlet, insert the gastroscope, and navigate back to the stomach cavity.

vii. OPTIONAL: Insufflate the stomach with air/inert gas to provide greater endoscopic visual working volume.

viii. Collapse the gastric implant and insert the lubricated implant into the over-tube, with inflation catheter following if required.

ix. Under endoscopic vision, push the gastric implant down the over-tube with gastroscope until visual confirmation of deployment of the device into the stomach can be determined.

x. Remove the guide-wire from the inflation catheter is used.

xi. If inflated: Inflate the implant using a standard Bio-Enterics Intragastric Balloon System ("BIB System") Fill kit.

xii. Using 50-60 cc increments, inflate the volume to the desired fill volume.

xiii. Remove the inflation catheter via over-tube.

xiv. Inspect the gastric implant under endoscopic vision for valve leakage, and any other potential anomalies. Record all observations.

xv. Remove the gastroscope from over-tube.

xvi. Remove the over-tube from the patient.

End Point Criteria:

Weight Loss

Comprehensive Metabolic Panel (CMP)

HbA1C

Lipid Panel

Tissue Samples/Response

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, references may have been made to patents and printed publications in this specification. Each of the above-cited references and printed publications are individually incorporated herein by reference in their entirety.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A passive intragastric obesity treatment implant, comprising:
   a series of non-inflatable members each having a through bore, each of the members having a male and a female mating connector which permits each member to connect with another member, each of the members being sized such that it can be easily implanted and removed through the esophagus, the members together capable of taking up volume within the stomach of at least 400 ml and being made of a material that will resist degradation over a period of at least six months within the stomach; and a tether sized to pass through the through bores of the non-inflatable members, a distal end of the tether attaching to a distal one of the non-inflatable members such that the members can be pulled together by pulling the tether taut to cause the male and female mating connectors to couple, thus forming a relatively solid structure, wherein the male and female mating connectors of the members are configured such that the relatively solid structure formed after pulling the tether taut is a non-straight shape, and wherein adjacent non-inflatable members in the series include features that cause the adjacent non-inflatable members to couple with each other in a predefined orientation relative to each other and without being able to move freely relative to one another.

2. The implant of claim 1, wherein the non-straight shape is a helix.

3. The implant of claim 1, wherein the members are no wider than 20 mm.

4. The implant of claim 1, wherein the rotational orientation of any one member relative to another is unrestricted when any one member is not coupled in the predefined orientation relative to the other.

5. The implant of claim 1, wherein each member is configured to only join together in a particular rotational orientation with another member.

6. The implant of claim 1, wherein each of the non-inflatable members comprises a body having an opening on one side centered about a radial axis and leading to an internal cavity that narrows into the internal through bore that angles within the spherical body and continues outward through a nipple projecting from another side along a different radial axis, wherein each nipple fits within a cavity of another of the members, and wherein each cavity has a helical ledge that terminates in a small notch, while the nipple has a single protrusion along its length, such that when a nipple is introduced into a cavity and forced together, the members will rotate until the protrusion on the nipple seats in the notch.

7. A passive intragastric obesity treatment implant, consisting of:
   a plurality of identically-shaped, non-inflatable members linked in series, each of the members being sized such that it can be easily implanted and removed through the esophagus, and being made of a material that will resist degradation over a period of at least six months within the stomach, wherein the series of members are configured to assume a particular non-straight shape when the series is placed under serial compression; and
   a tether configured to apply serial compression to the series of members,
   wherein the non-inflatable members each include a male mating connector and a female mating connector which permits each member to connect with another member.

8. The implant of claim 7, wherein the members together are capable of taking up a volume of at least 400 ml within the stomach.

9. The implant of claim 7, wherein adjacent non-inflatable members in the series include features that cause the adjacent non-inflatable members to mate with each other in a specific orientation relative to each other.

10. The implant of claim 7, wherein the tether has proximal and distal ends, wherein each of the non-inflatable members has a through bore, wherein the tether is sized to pass through the through bores of the non-inflatable members, and wherein a distal end of the tether attaches to a distal one of the series of non-inflatable members such that the members can be pulled together into serial compression by pulling the tether taut to cause the male and female mating connectors to couple.

11. The implant of claim 10, wherein when the tether is taut, the non-straight shape is a relatively solid structure.

12. The implant of claim 10, wherein the non-straight shape comprises a helix.

13. The implant of claim 10, wherein the throughbore angles within the non-inflatable member.

14. The implant of claim 13, wherein the non-inflatable member comprises a spherical body.

15. A passive intragastric obesity treatment implant, comprising:
   a series of non-inflatable members each having a through bore, the members each having a male and a female mating connector which permits each member to connect with another member, each of the members being sized such that it can be easily implanted and removed through the esophagus, the members together capable of taking up volume within the stomach of at least 400 ml and being made of a material that will resist degradation over a period of at least six months within the stomach; and a tether sized to pass through the through bores of the non-inflatable members, a distal end of the tether attaching to a distal one of the non-inflatable members such that the members can be pulled together by pulling the tether taut to cause the male and female mating connectors to couple, thus forming a relatively solid structure, wherein each of the non-inflatable members comprises a spherical body having an opening on one side centered about a radial axis and leading to an internal cavity, and a nipple projecting from another side.

16. The implant of claim 15, wherein the radial axis is angled relative to a different radial axis along which the nipple projects.

17. The implant of claim 15, wherein the cavity is stepped and narrows into the internal through bore that angles within the spherical body and continues outward through the nipple along a different radial axis, the nipple being stepped to fit within a stepped cavity of another of the members.

18. The implant of claim 17, wherein the axes aligned with the cavity and nipple define an obtuse included angle of between about 120-150°.

* * * * *